United States Patent
Joseph

(10) Patent No.: US 11,331,206 B2
(45) Date of Patent: May 17, 2022

(54) SUSPENDED SLEEVE ASSEMBLY COMPRISING A COMPRESSION SLEEVE AND A SUSPENSION STAND

(71) Applicant: Medical Creations, Inc., Aspen, CO (US)

(72) Inventor: Mark Joseph, Aspen, CO (US)

(73) Assignee: Medical Creations, Inc., Denver, CO (US)

( * ) Notice: Subject to any disclaimer, the term of this patent is extended or adjusted under 35 U.S.C. 154(b) by 0 days.

(21) Appl. No.: 16/516,199

(22) Filed: Jul. 18, 2019

(65) Prior Publication Data

US 2021/0015642 A1    Jan. 21, 2021

(51) Int. Cl.
*A61F 2/80* (2006.01)
*A61F 2/76* (2006.01)
(Continued)

(52) U.S. Cl.
CPC ............ *A61F 2/80* (2013.01); *A61F 2/5046* (2013.01); *A61F 2/60* (2013.01); *A61F 2/76* (2013.01); *A47G 25/905* (2013.01); *A61F 2002/5053* (2013.01); *A61F 2002/607* (2013.01); *A61F 2002/7868* (2013.01)

(58) Field of Classification Search
CPC . A47G 25/905; A61F 2002/7868; A61F 2/76; A61F 2/80; A61F 2002/607
See application file for complete search history.

(56) References Cited

U.S. PATENT DOCUMENTS

| 4,019,505 A | 4/1977 | Wartman |
| 4,704,129 A | 11/1987 | Massey |

(Continued)

FOREIGN PATENT DOCUMENTS

| WO | 2014182537 A1 | 11/2014 | |
| WO | WO-2017144604 A1 * | 8/2017 | ........... A61F 2/7812 |

OTHER PUBLICATIONS

Bracken S., "Graduate Student Works to Make Prosthetics Accessible in Developing Countries," PennState News, Feb. 2, 2016, 5 pages, https://news.psu.edu/story/390530/2016/02/02/academics/graduate-student-works-make-prosthetics-accessible-developing.
(Continued)

*Primary Examiner* — Javier G Blanco
(74) *Attorney, Agent, or Firm* — Messner Reeves LLP; Scott J. Hawranek

(57) ABSTRACT

A suspended sleeve assembly includes a suspension stand and a compression sleeve. An upper portion of the compression sleeve is attached onto the suspension stand, but a lower portion of the compression sleeve is unattached from the suspension stand. The suspended sleeve assembly can also include a support stand. The suspended sleeve assembly can be used to shape a prosthetic socket. The compression sleeve applies a circumferential pressure onto the prosthetic socket as the prosthetic socket is being inserted into the compression sleeve as a patient steps into the compression sleeve and applies at least a portion of body weight to the compression sleeve. The prosthetic socket can be heated and shaped by hand, so that it fits the residual limb of the patient. The suspended sleeve assembly can also be used to shape other prosthetic components, such as a negative plaster cast.

19 Claims, 12 Drawing Sheets

(51) Int. Cl.
*A61F 2/50* (2006.01)
*A61F 2/60* (2006.01)
A47G 25/90 (2006.01)
A61F 2/78 (2006.01)

(56) References Cited

U.S. PATENT DOCUMENTS

| | | | |
|---|---|---|---|
| D336,519 S | 6/1993 | Greene et al. | |
| 5,376,127 A | 12/1994 | Swanson | |
| 5,824,111 A | 10/1998 | Schall et al. | |
| 5,885,509 A | 3/1999 | Kristinsson | |
| 5,980,803 A | 11/1999 | Slemker et al. | |
| D429,335 S | 8/2000 | Caspers et al. | |
| D456,900 S | 5/2002 | Daftary | |
| D462,768 S | 9/2002 | Meyer et al. | |
| 6,444,282 B1 | 9/2002 | Shirer | |
| D477,875 S | 7/2003 | Meyer et al. | |
| D499,487 S | 12/2004 | Bedard et al. | |
| 6,869,560 B1 | 3/2005 | Drouin et al. | |
| 8,303,527 B2 | 11/2012 | Joseph | |
| 8,528,796 B1* | 9/2013 | Bosko | A47G 25/905 |
| | | | 223/112 |
| D748,791 S | 2/2016 | Kampas et al. | |
| D748,792 S | 2/2016 | Kampas et al. | |
| D778,452 S | 2/2017 | Cespedes et al. | |
| 9,635,967 B1* | 5/2017 | Hopper | A47G 25/90 |
| D798,453 S | 9/2017 | Cheng et al. | |
| 2008/0004716 A1 | 1/2008 | Hoerner | |
| 2008/0269914 A1 | 10/2008 | Coppens et al. | |
| 2014/0025183 A1 | 1/2014 | Kelley et al. | |
| 2014/0207253 A1* | 7/2014 | Horton | A61F 2/76 |
| | | | 623/33 |
| 2015/0265434 A1 | 9/2015 | Hurley et al. | |
| 2016/0143752 A1 | 5/2016 | Hurley et al. | |
| 2019/0053917 A1* | 2/2019 | Mosler | A61F 2/50 |

OTHER PUBLICATIONS

Dupere, K., "The 12 Most limpressive Social Good Innovations from June," Mashable, Jul. 1, 2016, 10 pages, [Online] [Retrieved on Aug. 20, 2019],URL: https://mashable.com/2016/07/01/social-good-innovations-june-2016.

International Search report and Written Opinion issued in International Application No. PCT/US2019/020484, dated Jun. 7, 2019, 12 pages.

International Preliminary Report issued in Application No. PCT/US2019/020484, dated Sep. 17, 2020, 11 pages.

Kemp, T., "Affordable, Adjustable Socket in the Works for Amputees in Need," O&P News, Jun. 1, 2016, 5 pages, [Online] [Retrieved on Aug. 20, 2019] URL: http://oandpnews.org/2016/06/01/affordable-adjustable-socket-in-the-works--for-amputees-in-need/>.

Wilson Jr., A.B., "A Material for Direct Forming of Prosthetic Sockets,"Artificial Limbs, 1970, vol. 14 (1), pp. 53-56.

Zhe., et al., U.S. Appl. No. 61/820,233, filed May 7, 2013.

Extended European Search Report issued in European Application No. 20190765111, dated Jan. 12, 2022, 11 pages.

* cited by examiner

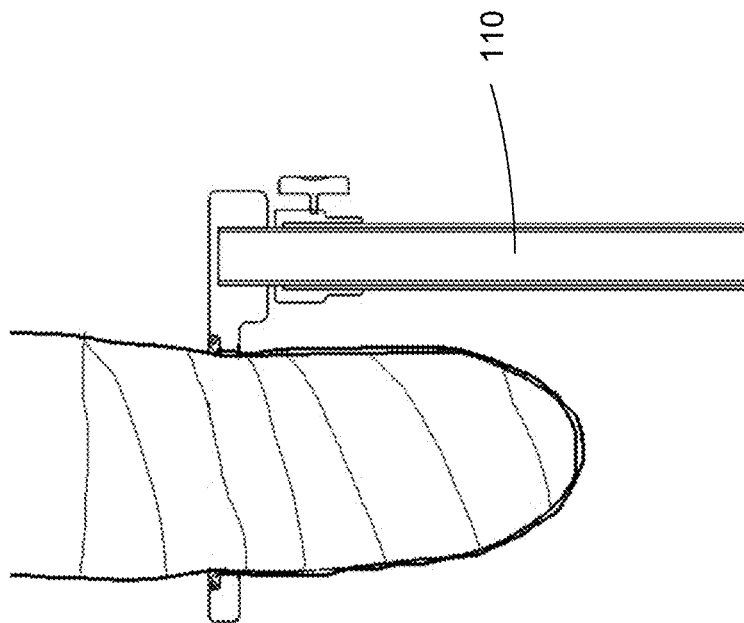
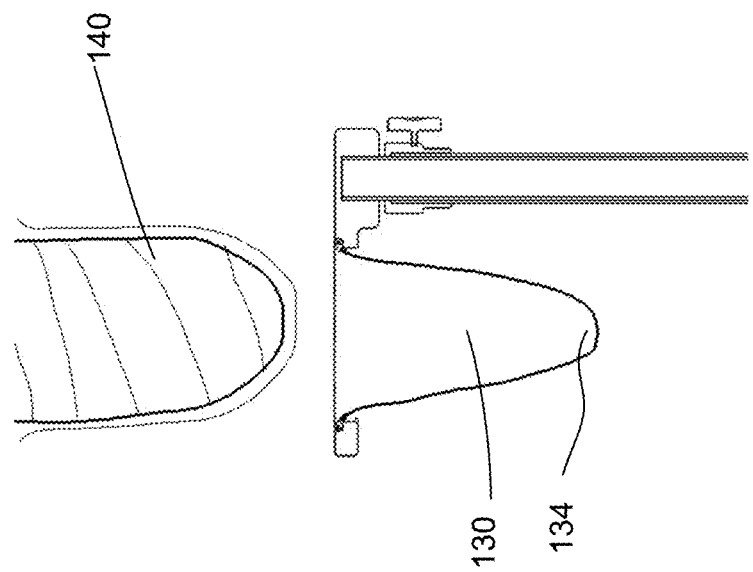
FIG. 7

SUSPENDED SLEEVE ASSEMBLY COMPRISING A COMPRESSION SLEEVE AND A SUSPENSION STAND

FIELD

The present disclosure generally relates to a suspended sleeve assembly that includes a compression sleeve and a suspension stand.

BACKGROUND

Fitting a prosthetic socket to an amputated limb is a critical step in the process of making a prosthesis for a patient. The work is carried out by prosthetists, and typically requires a high degree of training and experience. Prosthetic sockets are individually custom made, and typically constructed after either making a plaster mold and positive model of the residual limb or using laser scanning to produce images of the residual limb and using the mold or the images to produce a model. Additionally, sockets can be pre-made of materials that are on-body molded directly to the patient such as polymers, resins and heat activated materials.

Once the shaping process is complete, sockets made from limb models are formed by heating high temperature thermoplastics and forming them over the model using complicated and inefficient techniques. They may also be formed over the model using composite carbon fiber and resin. The process is time-consuming, wasteful, toxic, and often results in an imprecise fit to the residual limb that is difficult to adjust. The patient is typically required to make several visits to the prosthetist in this process and may bear a great deal of pain if the socket does not fit properly.

In the case of recent amputees, the residual limb is very sensitive, and over the period of months, can atrophy and shrink substantially, change shape, and develop callus. During this time, temporary "test" sockets are made using the above process, yet frequently with less durable materials because the sockets may only be worn for a short period until a subsequent one, started from scratch, is needed. This process may be repeated from three to five times depending on the amputation and amputee conditions, thereby significantly increasing the time, effort, waste, office visits, travel and efforts required of all involved. Any device or method that can improve this stressful, painful, time consuming, and often expensive experience for the amputee is of value.

The customary method for fitting and creating sockets starts by making a plaster impregnated fabric cast of the residual limb. It is done while the patient wears a common gel/fabric liner over the limb which protects the skin, holds the limb to the socket and is worn daily with the socket. Casting is done in a similar fashion to casting broken bones. A plaster impregnated fabric strip is soaked in water and wrapped over the limb liner typically covered with a plastic bag. As the plaster cures, the prosthetist uses the hands to shape and smooth the plaster as it sets. As final setting approaches, the most critical shaping occurs so it holds the contours during the final cure. This procedure requires a great deal of hand skill and touch by the prosthetist and experience in order to achieve the proper fit. Without the proper fit, the socket (and artificial limb) will not fit properly and the patient is likely to be in pain as described above. After curing, the cast and plastic bag are removed and the resulting positive model is adjusted in shape by the prosthetist by grinding and sanding. Subsequent test sockets or definitive sockets are made from this model. In some cases, the plaster cast is digitized, and a computer model is manipulated and transferred to a computer controlled milling machine to make the model.

Other socket building techniques involve applying a pre-made heated polymer socket that has become pliable and is on-body molded directly to the limb avoiding the plaster process. This on-body forming also reduces the imprecise hand grinding and shaping method currently used to adjust the model and eliminates forming the final high temperature plastic or composite/resin socket to the model. When cooled, the socket becomes rigid and can then be cut to size and finished in the normal manner. This saves time and provides a direct on-body fit which may be more precise and comfortable.

The aforementioned procedures are typically done while the patient is sitting and facing the practitioner with the leg extended in a non-weight bearing manner. Casting or molding are not typically done with the patient load bearing on the limb, which would mimic limb shape while standing or walking. Thus, there has been a desire for prosthetists to plaster cast or on-body mold sockets to patients while standing and bearing some degree of body weight on the limb.

In order to achieve a tight and precise fit of the plaster cast or on-body molded socket to the contours of the limb, applying circumferential pressure over the plaster cast or on-body molded socket can aid in precise forming and shaping. Past devices have incorporated this circumferential pressure using air or water pressure. However, these devices are bulky, complicated, expensive and prevent the prosthetist from applying the critical hand shaping to the cast or on-body molded socket as it cures or hardens.

Achieving a tight and precise fit requires the prosthetist to carefully evaluate the residual limb, alignment, stance and sensitivities, and determine the desired load bearing characteristics of the socket. Fitting the socket while the patient is sitting, and the residual limb is relaxed requires some degree of practitioner interpretation and estimation to properly form the model for maximum comfortability, since the shape and sensitivities of the residual limb may shift when the patient moves into standing position. Therefore, improved devices and methods are needed for forming prosthetic sockets, particularly to the lower limbs that allow weight bearing in addition to applying compression.

SUMMARY

The present disclosure relates to a suspended sleeve assembly that includes a suspension stand and a compression sleeve. The compression sleeve includes an upper portion attached onto the suspension stand and a lower portion that is unattached from (not attached to or free from) the suspension stand such that it is suspended from the suspension stand. The compression sleeve is configured to enclose at least a portion of a prosthetic socket worn by a patient when the prosthetic socket is inserted into the compression sleeve. The compression sleeve is also configured to allow the prosthetic socket to be shaped based on a shape of a residual limb of a patient wearing the socket.

In some embodiments, the compression sleeve includes a first and second ring (or other type of support or circumferential frame), and a receptacle. The first ring is located at the upper portion of the compression sleeve and is configured to attach the compression sleeve onto the suspension stand. The second ring is located at the lower portion of the compression sleeve and configured to secure the prosthetic socket in the compression sleeve. The receptacle is configured to receive and enclose a portion of the prosthetic socket. For example, the socket can be inserted into an opening at the upper portion of the sleeve (that can be defined by the first ring) such that it enters the receptacle of the sleeve, and it can be inserted until it reaches the lower portion or base of the sleeve (e.g., where the second ring is located).

In some embodiments, the suspension stand includes a base, a support pole, a height adjustor, and a ring. The base, or structure upon which the suspension stand sits on a surface, is at a lower portion of the suspension stand. The support pole is attached to the base and extends upward from the base (e.g., perpendicular to the base). The height adjustor is attached to the support pole and allows a user to adjust a height of the suspension stand based on a height of a patient wearing the prosthetic socket. The ring is at an upper portion of the suspension stand. The ring is attached to the support pole and configured to attach the upper portion of the compression sleeve onto the suspension stand.

A method for shaping a prosthetic socket by using a suspended sleeve assembly is also disclosed, and it includes providing a compression sleeve that comprises an upper portion attached to a suspension stand, a lower portion that is unattached from (not attached to or free from) the suspension stand, and a receptacle. The method further includes allowing a patient wearing the prosthetic socket to step into the compression sleeve attached to the suspension stand so that at least a portion of the prosthetic socket is enclosed in the receptacle of the compression sleeve. The method further includes adjusting a height of the suspension stand based on a height of the patient. The method also includes shaping the prosthetic socket through the compression sleeve based on a residual lower limb of the patient that is surrounded by the prosthetic socket.

BRIEF DESCRIPTION OF THE DRAWINGS

The teachings of the embodiments can be readily understood by considering the following detailed description in conjunction with the accompanying drawings.

FIG. 7 illustrates a plaster mode inserted into the suspended sleeve assembly of FIG. 1, in accordance with one embodiment.

DETAILED DESCRIPTION OF THE ILLUSTRATED EMBODIMENTS

Figure 1:
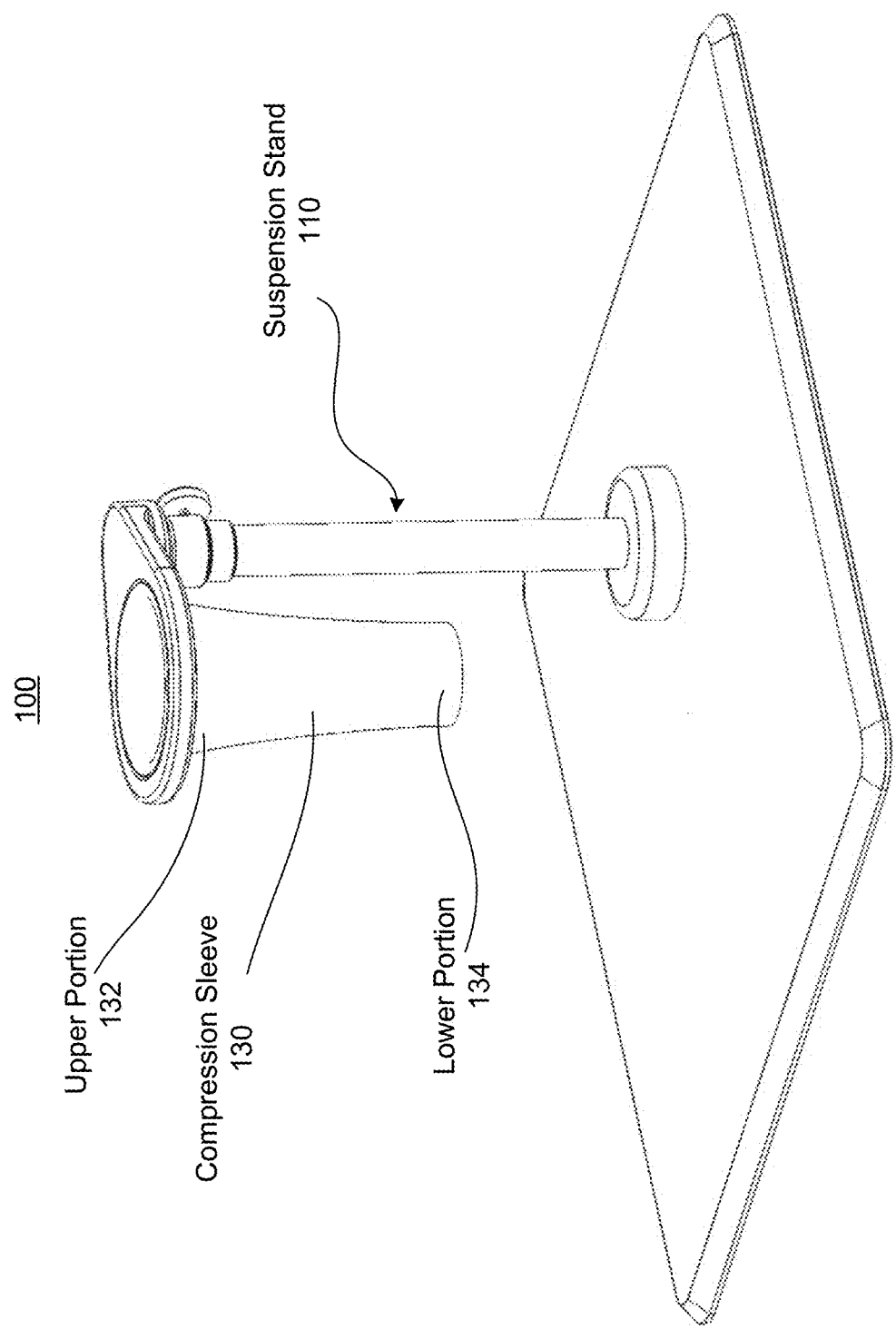
FIG. 1 is a perspective view of a suspended sleeve assembly comprising a compression sleeve and suspension stand, in accordance with one embodiment.

Persons skilled in the art will readily appreciate that various aspects of the present disclosure can be realized by any number of methods and articles configured to perform the intended functions. Stated differently, other methods and articles can be incorporated herein to perform the intended functions. It should also be noted that the accompanying figures referred to herein are not all drawn to scale but may be exaggerated to illustrate various aspects of the present disclosure, and in that regard, the figures should not be construed as limiting. Finally, although the present disclosure may be described in connection with various principles and beliefs, the present disclosure should not be bound by any theory.

Suspended compression sleeves, suspension stands, and methods in accordance with the present disclosure are used for fitting a plaster cast or on-body molded prosthetic socket to a residual limb of a patient, while the patient is in a standing position.

The present disclosure describes the use of a compression sleeve to apply pressure during the fitting process of a prosthetic socket to mount an artificial limb. The compression sleeve provides sufficient pressure to allow a prosthetist to use her hands and custom mold the prosthetic socket to the patient's residual limb to achieve the best fit. The compression sleeve is typically a thin material, such as knit fabric containing a spandex material or a woven material that can apply compression force when stretched over the prosthetic socket. In some embodiments, the compression sleeve functions in a way similar to a "Chinese hand cuff." can be a woven diagonal material that provides compression as it is stretched In one exemplary embodiment, the compression sleeve is suspended on a stand and hangs downward allowing the patient to step into the compression sleeve with the prosthetic socket in place and apply gravitational pressure, and further allowing the prosthetist to form and fit the prosthetic socket to the patient's residual limb. In this exemplary embodiment, the suspension stand supports the compression sleeve, such that the patient can place the residual leg with an on-body prosthetic socket (i.e., a prosthetic socket attached onto the residual leg of the patient) into the compression sleeve and apply standing pressure while the prosthetist molds the on-body prosthetic socket onto the limb. This allows forming or molding to be done while the patient is bearing weight, which better approximates the conditions and shape of the leg while standing and walking. The compression sleeve applies a circumferential compression force onto the prosthetic socket. The prosthetist can apply extra force onto the prosthetic socket with hands to form and fit the prosthetic socket to the patent's residual limb.

In another embodiment, the compression sleeve can be used to shape a negative plaster cast, such as a wet plaster cast. The compression sleeve encloses a negative plaster cast that is later used to form a positive model. For example, the negative plaster cast is formed over the amputated limb. This negative plaster cast is commonly plaster casting fabric impregnated with plaster that is wetted and wrapped on the residual limb to mimic the shape and dimensions of a patient. Other casting materials can be used. For example, a negative plaster cast can be made such that the limb can fit inside it cast, and then this can be used to make a shape that fits inside the negative cast and generally matches the residual limb. This is commonly done by lining the cast with a plastic bag and pouring in plaster—this is the positive model which is later used to form the prosthetic socket. The compression sleeve applies circumferential pressure onto the cast as it is shaped with the hands by the practitioner. Additionally, weight can be born by the patient onto the compression sleeve to simulate the condition of the limb under normal use while the cast is shaped.

The suspension stand in accordance with the present disclosure comprises a receiver for holding the compression sleeve in place that is adjustable in height. The receiver is of an appropriate size for stably holding the compression sleeve in place while the patient steps into it. The receiver can be formed with a hole. The hole may be sized to allow the largest common amputated limb to fit through it. The hole may be made in different sizes to fit limbs of various sizes. The receiver may be of a shape similar to the on-body molded socket or the patient's residual limb.

The receiver portion of the suspension stand is attached along the vertical axis of a support pole. The receiver of the suspension stand is height adjustable along the vertical axis of the support pole to accommodate the heights of various patients such that the normal standing pressure is applied when the patient steps into the compression sleeve with a plaster cast or molded prosthetic socket that is to be molded while the patient is wearing it. The height of the receiver may also be slightly adjusted by moving the receiver along the vertical axis of the support pole while the patient is standing in the compression sleeve. For example, the receiver may be connected to the pole through a clamping mechanism that is loosened during adjustment along the pole, and securely re-tightened when the receiver is placed at the desirable height. Alternatively, the height of the support pole may be adjustable through a screw height adjuster or height adjusting knob. Various adjustable components to support the receiver portion can be used, such as a tripod, wall or other structures. Additionally, the support may be adjusted using components such as motors, hydraulics, air pressure and the like.

The compression sleeve that is engaged by the suspension stand can be made of various pliable materials, such as knit fabric, knit stretch fabric, diagonally woven fabric, fiber material, insulative material, rubber, urethane, polymer or other pliable materials. The compression sleeve may be made in various sizes and shapes to achieve different results. The compression sleeve includes a first attachment structure (such as a circumferential frame that can be a rigid ring, or a stand or other support) that is incorporated within the compression sleeve and located at the upper portion of the compression sleeve. The first attachment structure attaches the upper portion of the compression sleeve onto the suspension stand. The compression sleeve also has a second attachment at the lower portion. The second attachment structure secures the on-body molded prosthetic socket in the compression sleeve. The second attachment structure can be a circumferential frame, such as a rigid ring, closed end or can be a stand or other support. For making a plaster cast the end can be closed in a cupped shape to stretch and fit the distal end of the limb.

One function of the compression sleeve is to apply circumferential pressure to the plaster cast or on-body molded socket as it cures or hardens, thereby aiding in shaping and applying a tight fit during the process. The compression sleeve also serves to suspend the plaster cast or on-body molded socket so that the patient may bear weight into it. The compression sleeve may be constructed such that more circumferential pressure is applied as more weight is applied, similar to a "Chinese handcuff" toy, which locks the fingers together when pulled. Another feature of the compression sleeve is to insulate the on-body molded socket, which is heated for forming. This heat insulation extends the working time of the prosthetic socket, as well as insulates the prosthetist allowing more accurate shaping without gloves.

The method according to various exemplary embodiments in the present disclosure comprises inserting the residual limb with a gel liner into the plaster cast or on-body molded socket and inserting it into the compression sleeve supported by the suspension stand. Then downward weight is applied while the plaster cast or on-body molded socket is manipulated and shaped (e.g., with hands of a prosthetist) as it hardens. The prosthetist can then form the shape directly to the residual limb while the patient is load bearing.

The compression sleeve and related method can be used for a variety of prosthetic sockets and methods of fitting said prosthetic sockets to a patient. In certain exemplary embodiments the compression sleeve can be used for a variety of off-body forming using plaster molds or on-body forming where the prosthetic socket is directly fitted to the patient's residual leg. More specific and non-limiting examples include the OSSUR ice cast system produced by OSSURE HF of Reykjavik, Iceland, other existing heat formed premade sockets, and traditional methods of fitting a prosthetic socket using a plaster cast to make a negative form and positive plaster model.

In some embodiments, the prosthetic sockets fitted with the compression sleeve are formed from proprietary thermoplastic materials which allow the prosthetic sockets to be heat formed at higher temperatures than previously used. A prosthetic liner sufficiently thick and insulative to protect the residual limb from the higher temperatures is worn on the limb during forming of the prosthetic socket. Amputees commonly wear such liners to protect the residual limb and hold the prosthetic socket firmly to it. They can, for example, comprise stretchable gel with an outer stretch fabric lining. The gel may comprise silicone, polyurethane or other similar materials that are compatible with the skin and, using circumferential tightness, will hold firmly to the limb. Various attachment members may be used to hold the liner to the prosthetic socket, and sockets in accordance with the present disclosure may be compatible with such attachment members. Other suitable insulation types may include fabric liners comprising cotton, various foams, and other materials that are sufficiently insulative.

In various embodiments, the compression sleeve with or without the suspension stand is used to fit any of the prosthetic sockets disclosed in U.S. Ser. No. 15/914,480 entitled Prosthetic Limb Sockets and Methods of Making and Using, which is herein incorporated by reference in its entirety.

Figure 2:
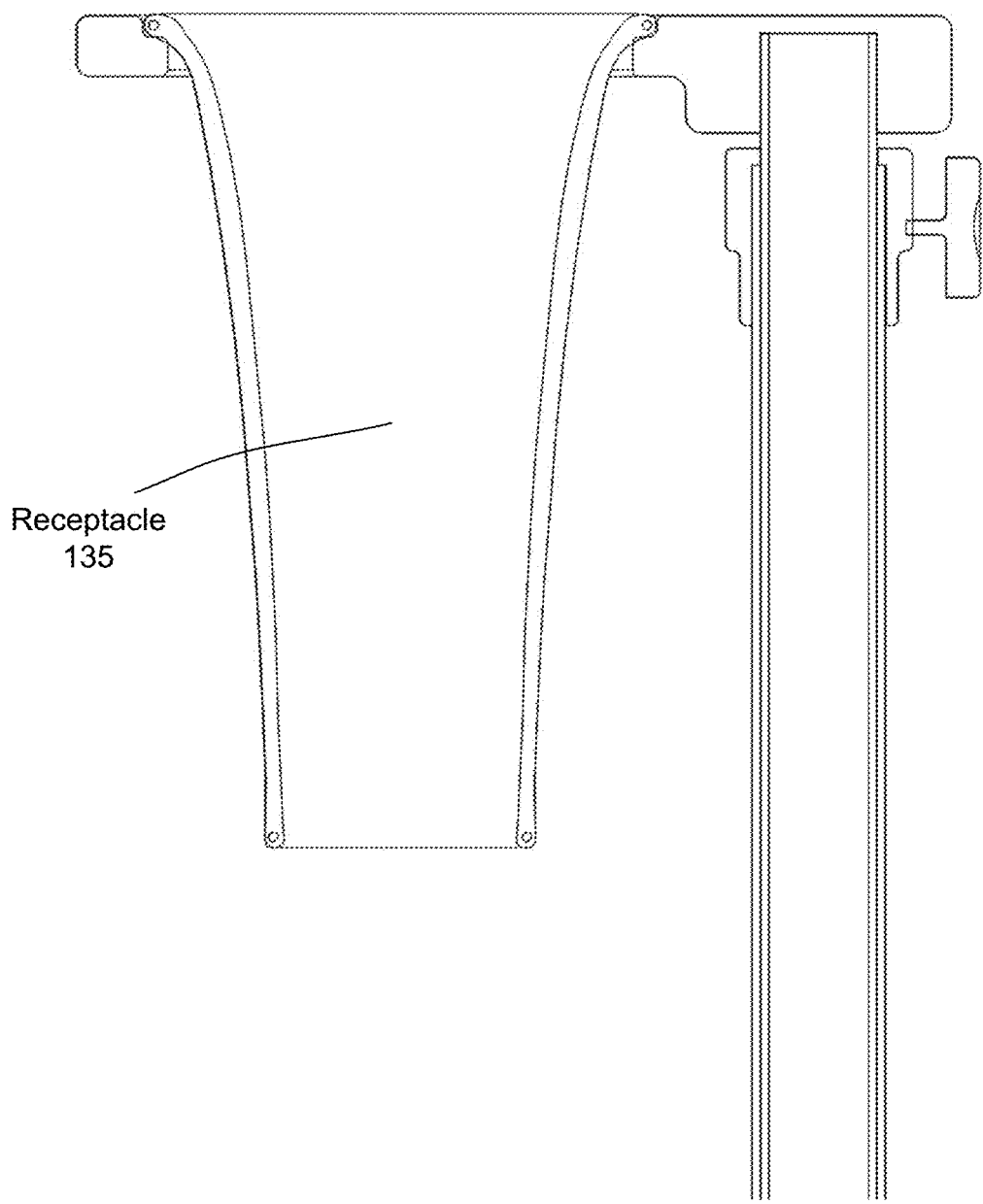
FIG. 2 is a cross-sectional view of the suspended sleeve assembly of FIG. 1, in accordance with one embodiment.
Figure 3:
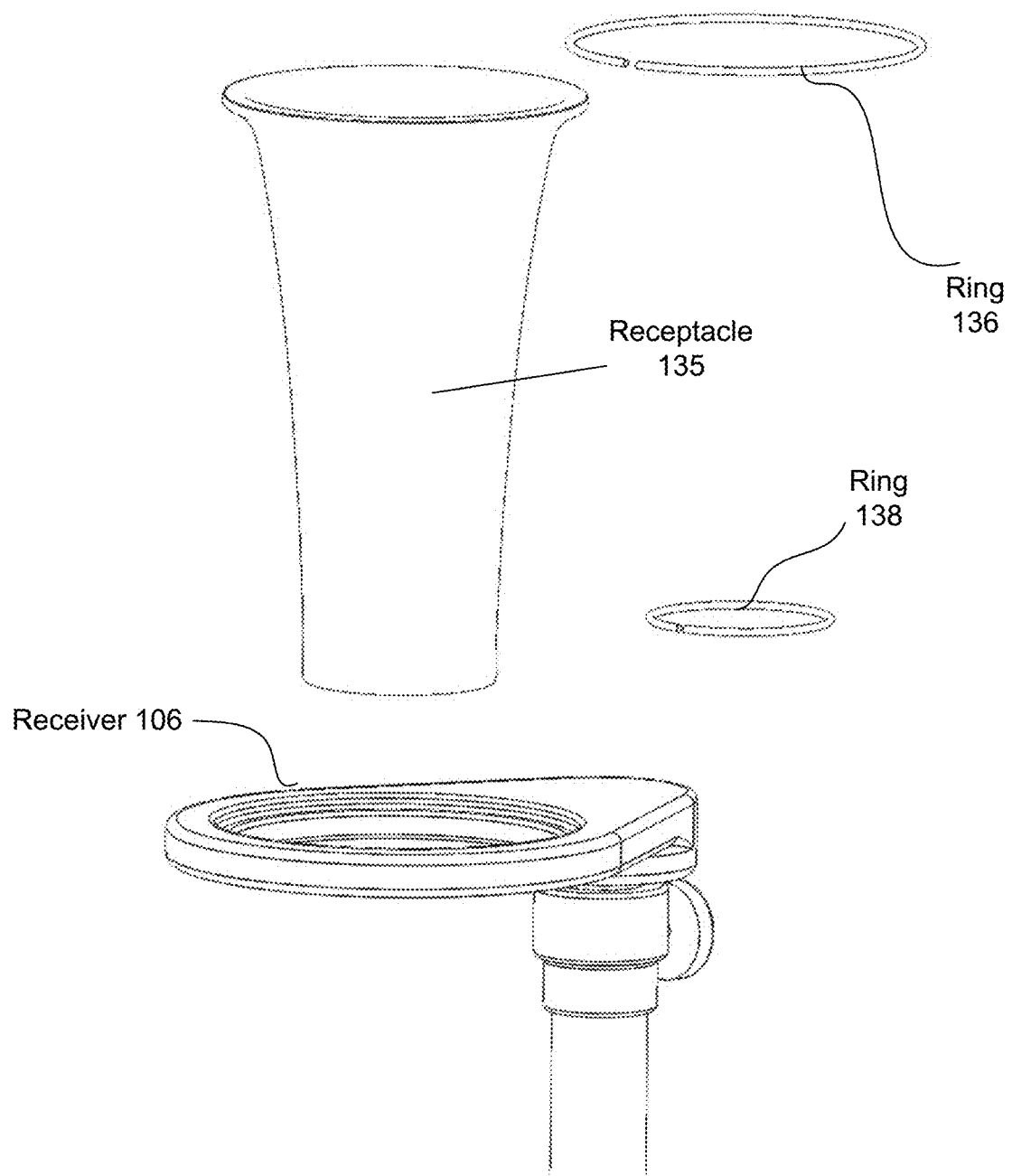
FIG. 3 is an exploded view of a portion of the suspended sleeve assembly of FIG. 1, in accordance with one embodiment.
Figure 4:
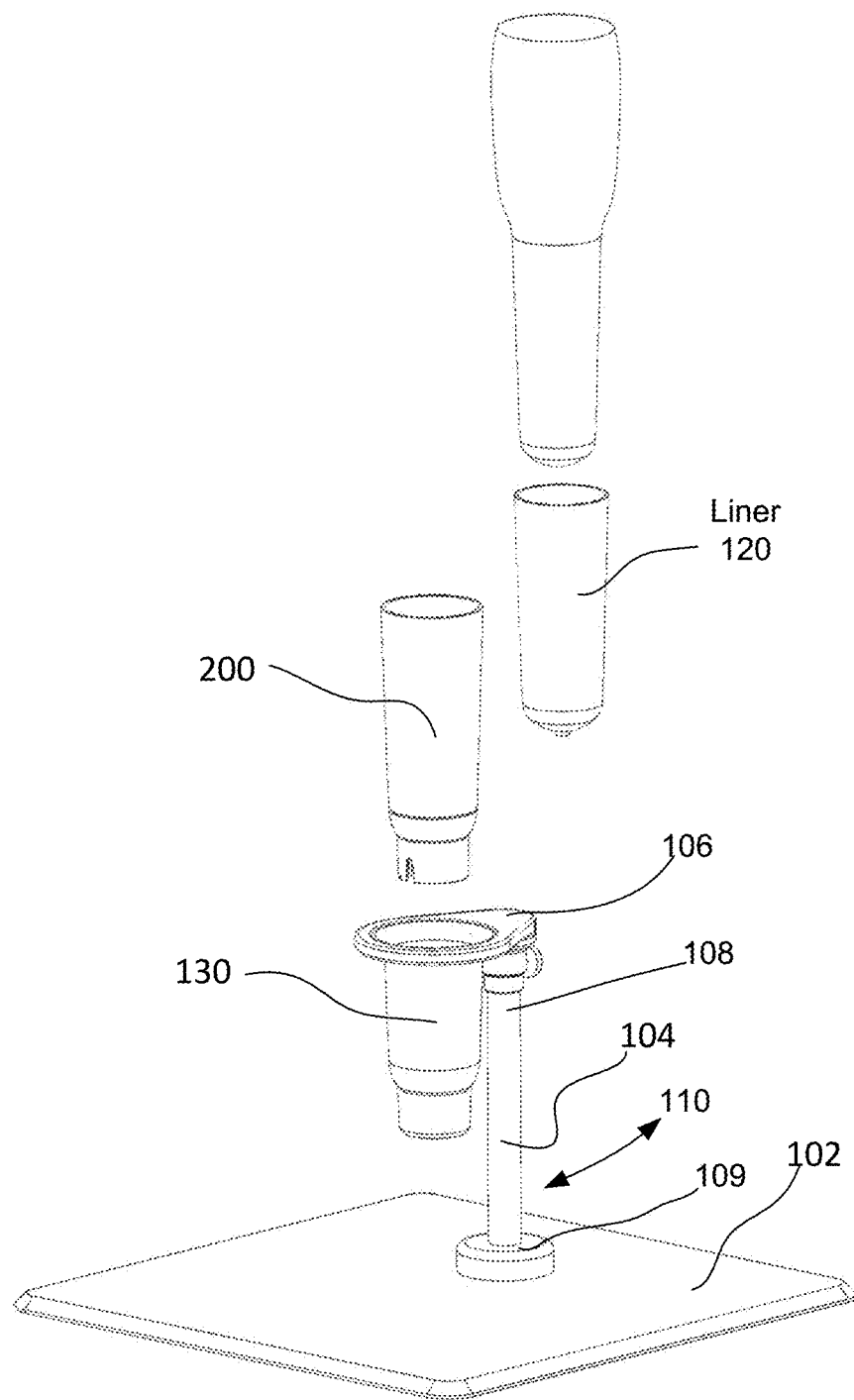
FIG. 4 illustrates a prosthetic socket to be inserted into the suspended sleeve assembly of FIG. 1, in accordance with one embodiment.
Figure 5:
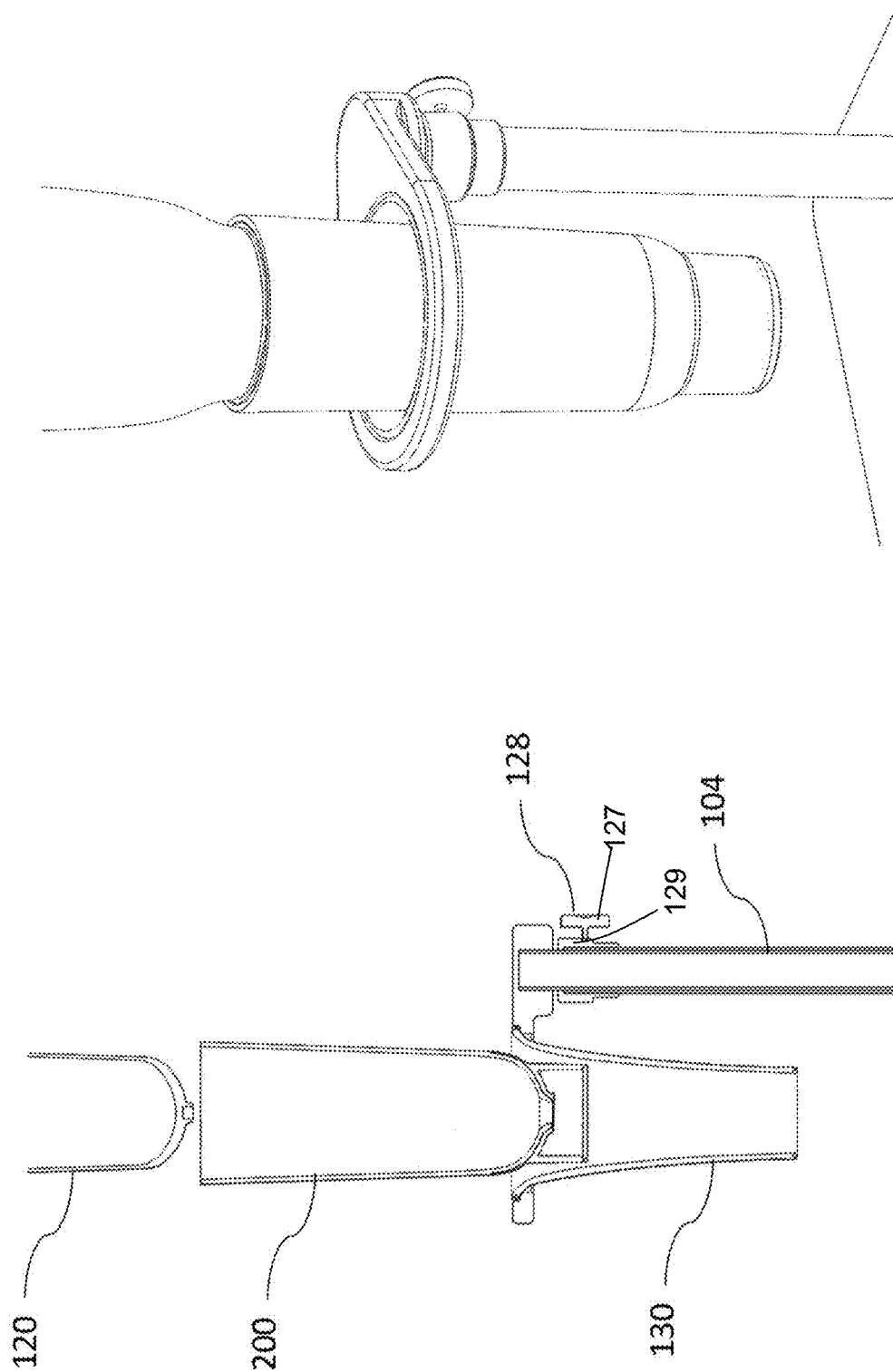
FIG. 5 illustrates a prosthetic socket inserted into the suspended sleeve assembly of FIG. 1, in accordance with one embodiment.

A suspended sleeve assembly 100 comprising a compression sleeve 130 and a suspension stand 110 in accordance with exemplary embodiments of the present disclosure is illustrated in FIGS. 1-5. FIG. 1 is a perspective view of a suspended sleeve assembly 100 comprising a compression sleeve 130 and suspension stand 110, in accordance with one embodiment. FIG. 2 is a cross-sectional view of the suspended sleeve assembly 100 of FIG. 1, in accordance with one embodiment. FIG. 3 is an exploded view of a portion of the suspended sleeve assembly 100 of FIG. 1, in accordance with one embodiment. FIG. 4 illustrates a prosthetic socket 200 to be inserted into the suspended sleeve assembly 100 of FIG. 1, in accordance with one embodiment. FIG. 5 illustrates a prosthetic socket 200 inserted into the suspended sleeve assembly 100 of FIG. 1, in accordance with one embodiment.

The compression sleeve 130 is configured to tighten circumferentially around the on-body molded socket 200 during elongation as the on-body molded socket 200 is inserted. The compression sleeve 130 has an upper portion 132 and a lower portion 134, with an opening at the upper portion 132 for receiving the plaster cast or on-body molded socket. The upper portion 132 is attached onto the suspension stand 110. The lower portion 134 is unattached from (detached or not connected to) the suspension stand 110 (though it is possible to have it connected at the lower portion for stabilization or other purposes). The compression sleeve 130 is configured to enclose at least a portion of the on-body prosthetic socket and to allow the on-body prosthetic socket to be shaped based on a shape of a residual limb of a patient wearing the on-body prosthetic socket. A liner 120 may be worn on the residual limb before insertion into compression sleeve 130. In some embodiments, compression sleeve 130 is cylindrical or conical in shape. In some embodiments, the upper portion 132 includes an attachment structure or circumferential frame, e.g., a top rigid ring 136 or stand, configured to suspend compression sleeve 130 from a structure, e.g., the suspension stand 110. In some embodiments, the lower portion 134 comprises an attachment structure or circumferential frame, e.g. a bottom rigid ring 138 or stand, configured to connect and stabilize the on-body molded socket. Further, in these embodiments, top rigid ring 136 and bottom rigid ring 138 are incorporated and contained within compression sleeve 130. The compression sleeve 130 also includes a receptacle 135 between the two attachment structures. The receptacle 135 encloses at least a portion of the on-body prosthetic socket. The receptacle 135 can apply pressure (e.g., circumferential pressure) onto the portion of the on-body prosthetic socket during the shaping of the on-body prosthetic socket. An end of the receptacle 135 may be closed or substantially closed. In some embodiments, dimensions (e.g., length, inner diameter, etc.) of the receptacle 135 are selected to fit the on-body prosthetic socket or the amputated limb of the patient. In some embodiments, the suspended sleeve assembly 100 includes a plurality of compression sleeves 130 having receptacles 135 of different dimensions to fit prosthetic sockets or amputated limbs of various sizes.

The receptacle 135 comprises an elastic material, such as knit fabric, woven material, woven fibers, stretch polymer, or some combination thereof. In some embodiments, the receptacle 135 is no more than three millimeters thick. In some embodiments, the receptacle 135 is no more than two millimeters thick. In one embodiment, the receptacle 135 is comprised of a knit fabric containing an elastic-like material such as spandex so that it applies compression force by stretching. In yet other embodiments, the receptacle 135 comprises a woven material that applies compression force as it is stretched. In this embodiment, the forces applied are similar to what occurs with so-called "Chinese hand-cuffs." In yet other embodiments, the receptacle 135 is comprised of stretch polymers. The receptacle 135 may also comprise material that shrinks in diameter as it is elongated according to various embodiments of the present invention.

In some embodiments, the compression sleeve 130 comprises handles at the upper portion 132 for the pulling compression sleeve 130 over the plaster cast or on-body molded socket. This enables the prosthetist to more easily apply compression sleeve 130 to the plaster cast or prosthetic socket 200.

In an exemplary embodiment, the compression sleeve 130 is attached to a suspension stand 110. As shown in FIGS. 1-7, the suspension stand 110 comprises a base 102, a support pole 104 having a upper portion 108 and a lower portion 109, and a receiver 106 configured to receive and stabilize compression sleeve, wherein the receiver 106 is connected to support the upper portion 108 of the support pole 104, wherein the compression sleeve 130 is suspended from and supported by the receiver 106. In various embodiments, the support pole 104 is height-adjustable for ease of fitting while the patient is in a natural standing position. In some embodiments, support pole 104 is height-adjustable using a height adjustor 128. The height adjustor 128 includes a knob 127 and a clamp 129 attached to the knob. The clamp 129 is attached to the receiver 106 so that the receiver 106 can move with the clamp 129. A user may turn the knob 127 to loosen the clamp 129 so that the receiver 106 can be moved up or down along the support pole 104. After the receiver 106 reaches an intended position, the user can turn the knob to tighten the clamp 129 to fix the receiver 106 on the support pole 104. In some embodiment, the receiver 106 is at a height that allows the patient to stand fully upright when the residual limb and prosthetic socket are inserted into the compression sleeve 130. In some embodiments, while the suspension stand 110 is in use, the receiver 106 is at a height that allows the patient to step into the compression sleeve 130 while wearing a prosthetic socket 200, and stand in a natural, comfortable position as a prosthetist molds the prosthetic socket 200 onto the residual limb. The height may be further adjusted while the patient is standing in the compression sleeve 130. Because of the compression force applied to the prosthetic socket 200 by compression sleeve 130, the prosthetist is able to use her hands solely to mold prosthetic socket 200 to the patient's residual limb without having to worry about sufficient pressure being applied to prosthetic socket 200 which allows the prosthetist to achieve a better fit and hence allow the patient to experience greater comfort. Further, in some embodiments, receiver 106 is vertically adjustable along the length of the support pole 104.

As shown in FIGS. 1-7, the support pole 104 is tube shaped. The support pole 104 can have other shapes, such as square, triangle, etc. The support pole 104 can be solid or hollow. In some embodiments, the suspension stand 110 comprises multiple support poles 104.

In some embodiments, other support structures besides the suspension stand 110 are used. For example, a tripod or wall configured to connect to the receiver 106 may be used as a support for the compression sleeve 130. Any known device that supports compression sleeve 130 can be used and fall within the scope of the present invention.

In yet another exemplary embodiment, the suspended sleeve assembly can comprise compression sleeve 130 alone without suspension stand 110. In these exemplary embodiments, compression sleeve can be fitted around prosthetic socket 200 or a plaster mold as described below. While attached to prosthetic socket 200 or a plaster mold, the prosthetist can mold prosthetic socket 200 or the plaster mold with her hands. For example, the prosthetic can hand-mold the prosthetic socket 200 onto the residual limb of a patient. This embodiment is particular useful in a situation where a patient has a hard time standing and the device must be fitted to them while the patient is sitting or lying down.

Further, the suspended sleeve assembly and method of the present invention can be used for a variety of prosthetic sockets 200 and methods of fitting them. For example, the suspended sleeve assembly and method according to the present invention can be used for traditional off-body methods of fitting a socket such as those comprising plaster molds. Alternatively, the suspended sleeve assembly and method of the present invention can be used for on-body forming of prosthetic sockets 200. Certain exemplary and non-limiting examples of prosthetic socket 200 that can be used include the OSSUR "ice cast" suspended sleeve assembly produced by OSSUR HF of Reykjavik, Iceland, the prosthetic sockets disclosed in U.S. Ser. No. 15/914,480, and various heat formed prosthetic socket 200 that are off body or on body molded.

Figure 6:
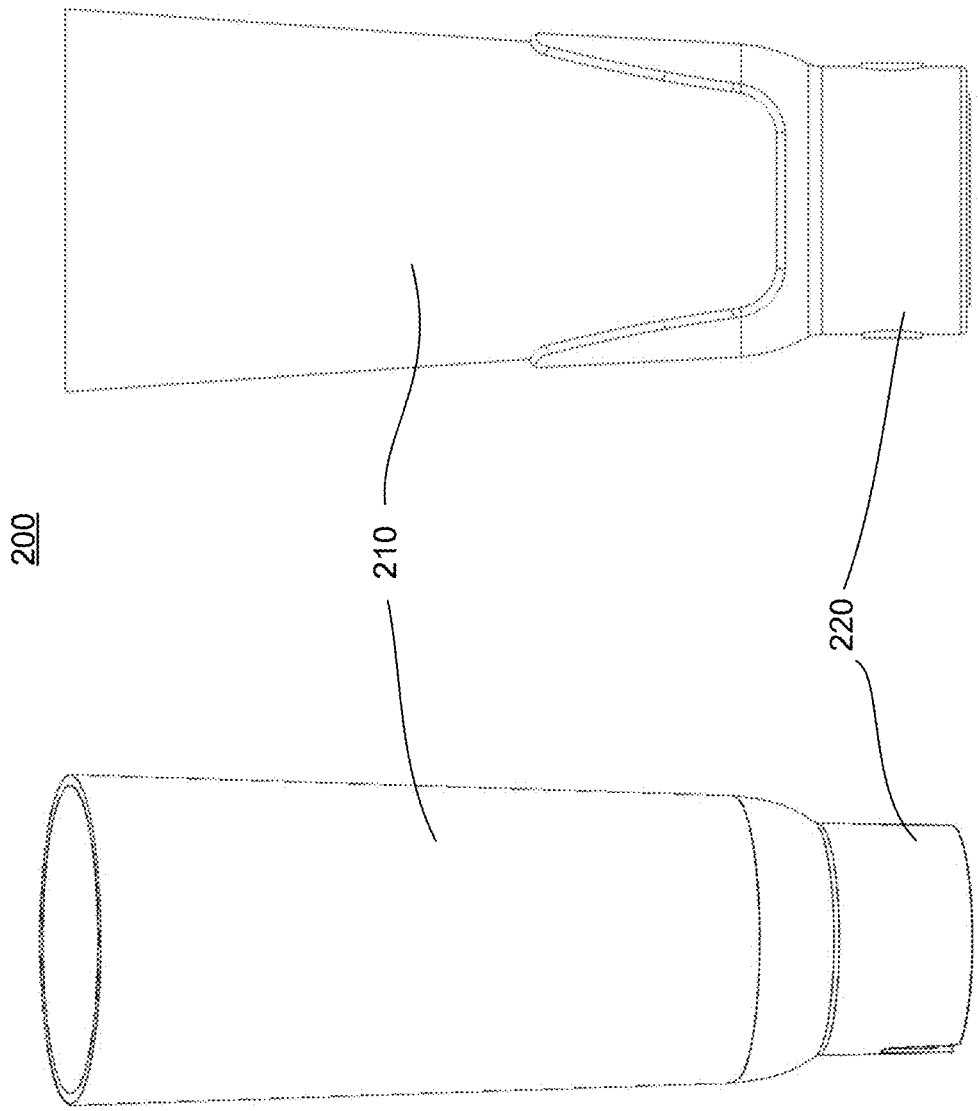
FIG. 6 illustrates a prosthetic socket, in accordance with one embodiment.

FIG. 6 illustrates a prosthetic socket 200, in accordance with one embodiment. FIG. 6 shows two configurations of the prosthetic socket 200. In some embodiments, the prosthetic socket 200 comprises a conical cup 210, coupled to a lower portion 220. Conical cup 210 is sized and configured to engage with a residual limb, securing prosthetic socket 200 to limb. As shown in FIGS. 1 and 3-6, a liner 120 may be worn on the residual limb. In such embodiments, conical cup 210 of prosthetic socket 200 surrounds liner 120. Liner 120 may help reduce chafing and discomfort between the residual limb and conical cup 210, as well as secure them together.

In some embodiments, conical cup 210 of prosthetic socket 200 has a first pliability in a given temperature range which is greater than the pliability of base portion 220 in the same temperature range. For example, in some embodiments conical cup 210 comprises a polymeric material having a pliability between about 160° F. and about 302° F. (between about 70° C. and about 150° C.), and further, between about 225° F. and about 275° F. (between about 107° C. and about 135° C.). In various embodiments, when heated to between about 160° F. and about 302° F. (between about 70° C. and 150° C.), the pliability of conical cup 210 provides a working time of between about five minutes and about 15 minutes before hardening. The pliability and working time allow conical cup 210 to be stretched circumferentially over the residual limb before conical cup 210 cools and re-hardens at a circumference that is reduced after the cooling and re-hardening process. When inserted into compression sleeve 130, the pliability and working time are increased due to the insulation of compression sleeve 130. Again, as noted above, the suspended sleeve assembly of the present invention can be used with the device and method disclosed in U.S. Ser. No. 15/914,480 entitled Prosthetic Limb Sockets and Methods of Making and Using.

In some embodiments, the suspended sleeve assembly and prosthetic socket are provided together as a kit for use by the prosthetist. The prosthetist uses the kit to shape the socket via the suspended sleeve assembly.

According to various exemplary embodiments, the method of using the suspended sleeve assembly of the present invention involves various steps. First, for an on-body molding technique, the patient will have prosthetic socket 200 loosely attached to his or her residual limb. Then, the patient will step into compression sleeve 130 as it is suspended within suspension stand 110. As the patient steps into compression sleeve 130 the patient's weight will press prosthetic socket 200 against the patient's residual limb with the gravitational force of the patient inserting prosthetic socket 200 into compression sleeve 130. This force is equivalent to what the patient would typically place on prosthetic socket 200 in a walking or standing position. As the patient applies gravitational force, the height adjustor 128 can be used to easily adjust support pole 104 to help ease the patient into a balanced, straight upright position. Once the patient is in this position, the prosthetist will hand mold the prosthetic socket 200 around the patient's residual limb without needing to press against or otherwise be concerned with the force of prosthetic socket 200, as compression sleeve 130 is applying this force while the patient is standing. The patient may be seated on a stool and apply partial body weight onto the compression sleeve 130 during the process. Alternatively, the patient may be in a standing position and apply normal body weight. The compression sleeve may provide sufficient pressure to enable the prosthetist to form and shape the prosthetic socket without having to apply additional pressure to the prosthetic socket.

In other exemplary embodiments, the suspended sleeve assembly of the present invention is used for more traditional methods of fitting prosthetic sockets which involve using negative plaster casts and positive plaster models. In this embodiment, Plaster casting tape 140 is wetted and wrapped onto the limb that has a plastic bag over it to protect the limb or liner.

FIG. 7 illustrates a plaster cast inserted into the suspended sleeve assembly of FIG. 1, in accordance with one embodiment. In FIG. 7, a plaster cast 140 is wrapped over the limb with known techniques, covered with a plastic bag, and then inserted into the compression sleeve 130. In some embodiments, the plaster cast 140 is inserted into the compression sleeve 130 and the prosthetist users her hands to form the mold in a manner similar to the on-body forming technique. In this embodiment, the patient may step into compression sleeve 130 which provides further compression automatically and helps shape the plaster cast 140. In this embodiment, compression sleeve 130 has an enclosed rounded lower portion 134 to support the plaster cast 140 and keeps it from falling out of the compression sleeve 130. As the patient applies gravitational force, the height adjustor 128 can be used to adjust the support pole 104 to help ease the patient into a balanced, straight upright position.

In this embodiment, the prosthetist will use the suspended sleeve assembly 100 to form plaster mold 140 in a similar fashion to what is used with the on-body forming embodiment described above. The difference is that in this embodiment, the sleeve is pressed around the plaster cast 140 as opposed to a prosthetic socket 200.

In some embodiments, the suspension stand 110 is omitted, and compression sleeve 130 is used to fit a prosthetic socket or plaster mold while the patient is in a standing, sitting, or prostrate position.

Figure 8:
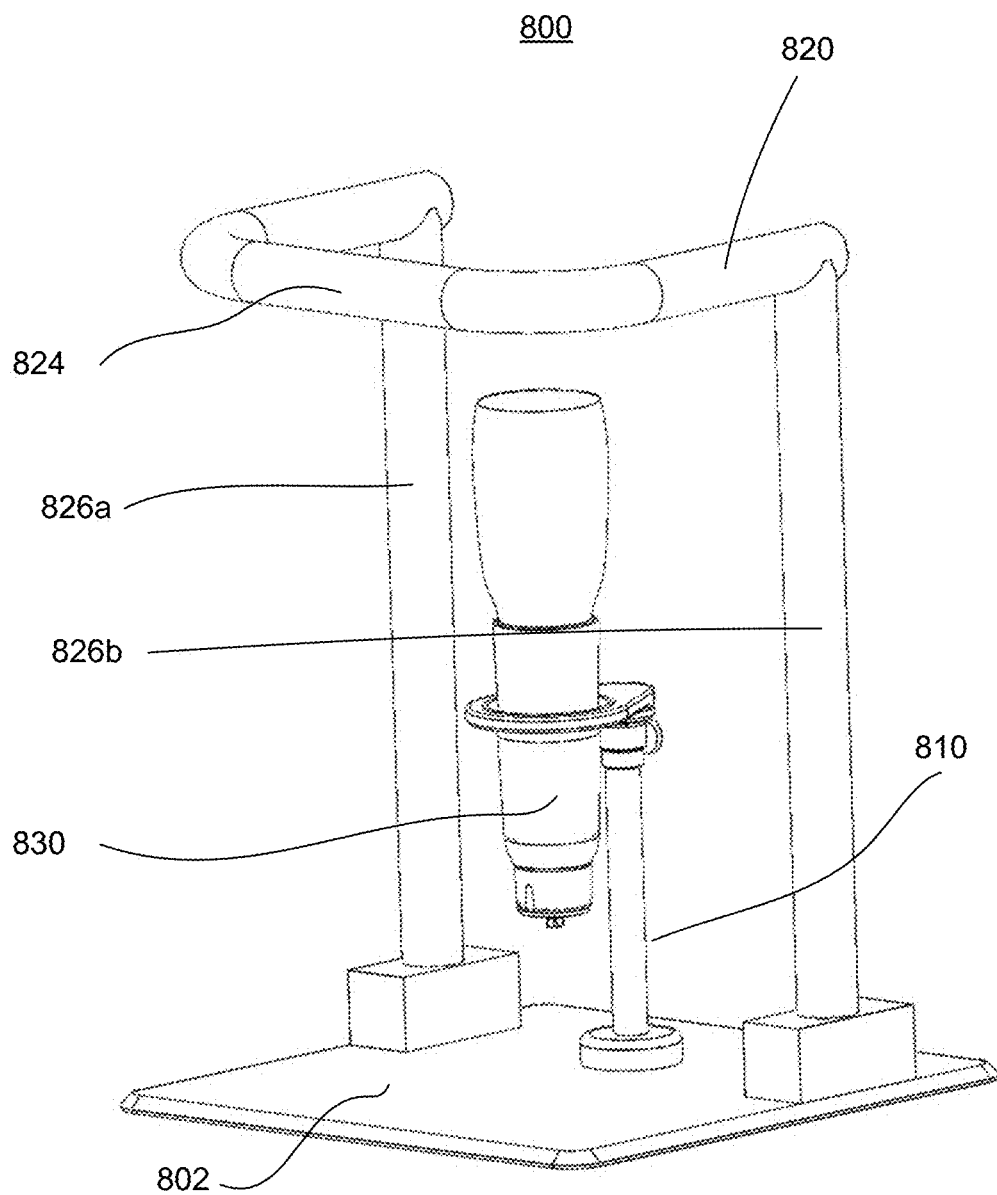
FIG. 8 is a perspective view of a suspended sleeve assembly comprising a compression sleeve, a suspension stand, and a support stand, in accordance with one embodiment.
Figure 10:
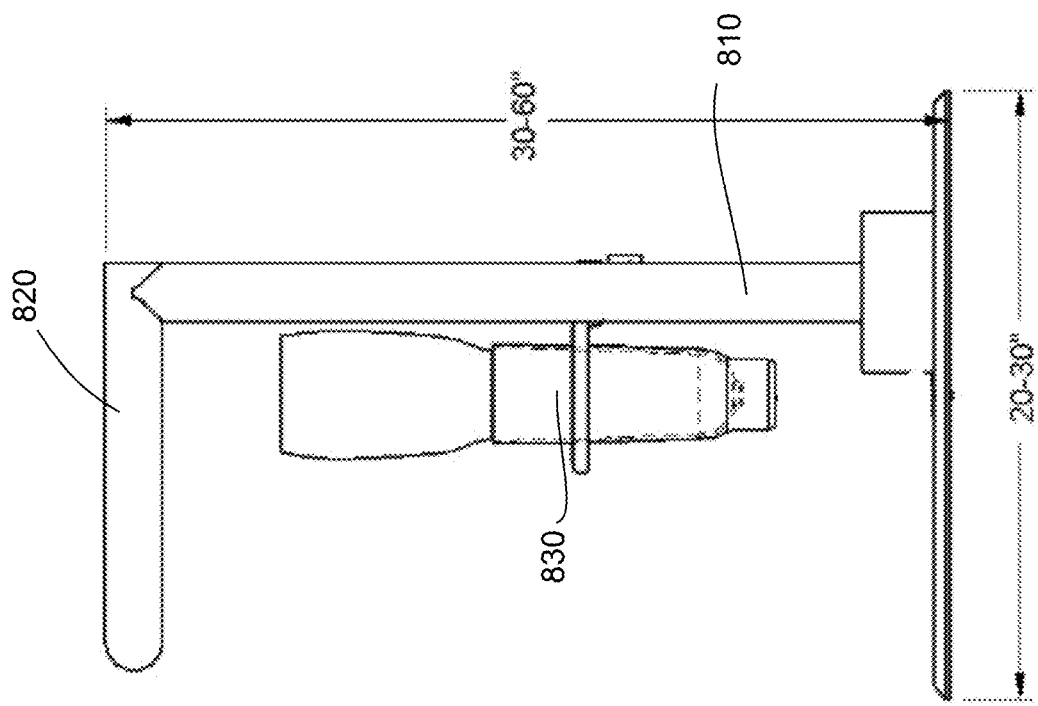
FIG. 10 is a front view of the suspended sleeve assembly of FIG. 8, in accordance with one embodiment.
Figure 9:
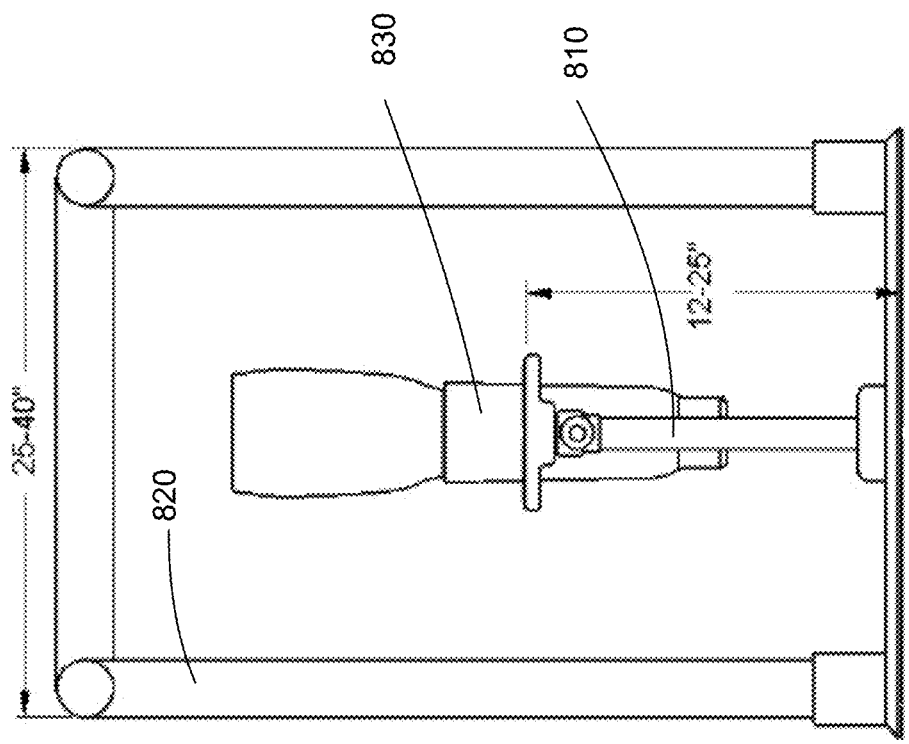
FIG. 9 is a side view of the suspended sleeve assembly of FIG. 8, in accordance with one embodiment.
Figure 11:
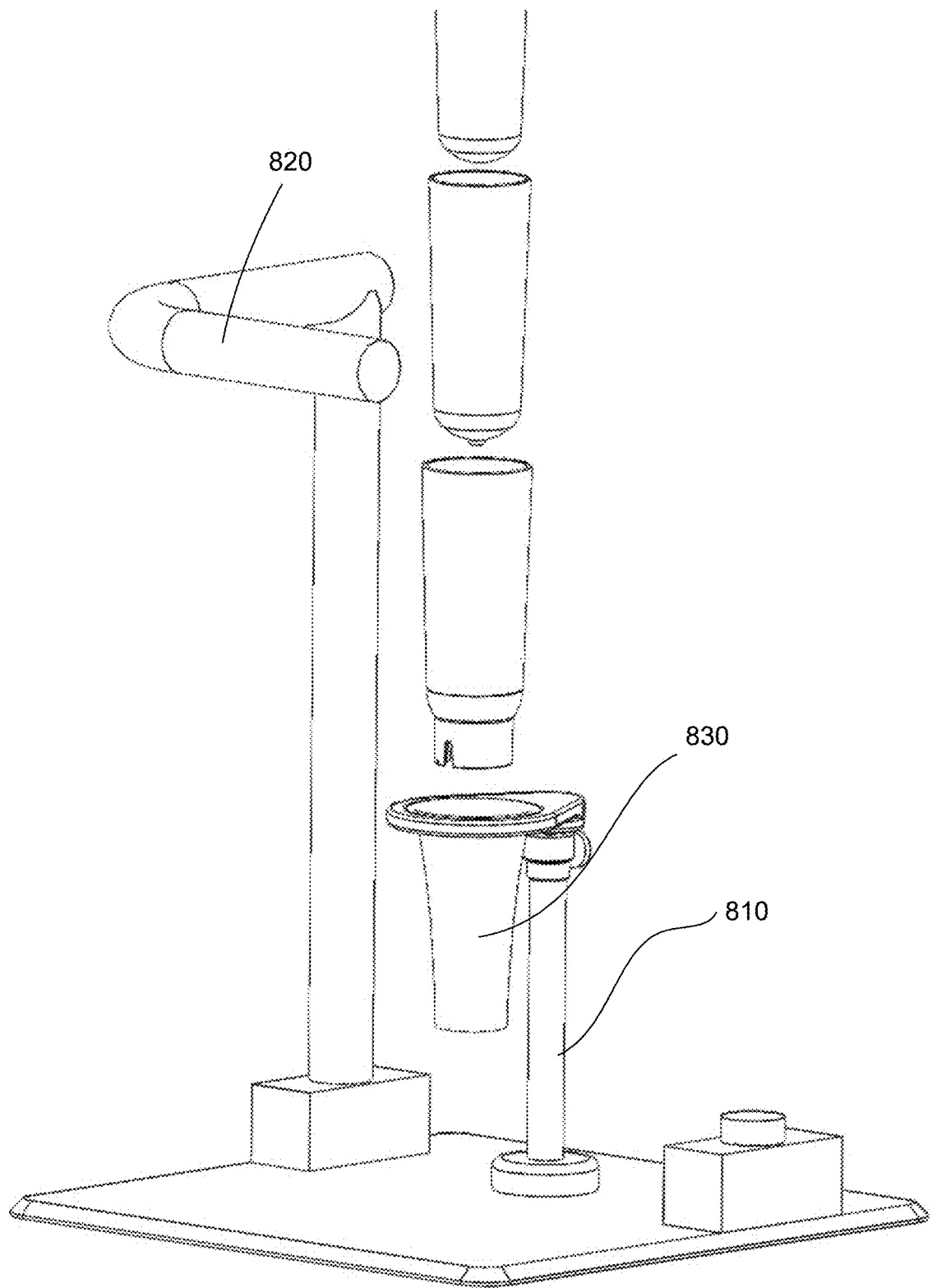
FIG. 11 illustrates a prosthetic socket to be inserted into the suspended sleeve assembly of FIG. 8, in accordance with one embodiment.

FIG. 8 is a perspective view of a suspended sleeve assembly 800 comprising a compression sleeve 830, a suspension stand 810, and a support stand 820, in accordance with one embodiment. FIG. 9 is a front view of the suspended sleeve assembly of FIG. 8, in accordance with one embodiment. FIG. 10 is a side view of the suspended sleeve assembly of FIG. 8, in accordance with one embodiment. FIG. 11 illustrates a prosthetic socket to be inserted into the suspended sleeve assembly of FIG. 8, in accordance with one embodiment. The compression sleeve 830 can be the compression sleeve 130 described in conjunction with FIGS. 1-7. The suspension stand 810 can be the suspension stand 110 described in conjunction with FIGS. 1-7.

The support stand 820 provides support to the patient as the patient steps into the compression sleeve 830. By using the support stand 820, the patient can have balance and stabilization and is about waist height. The support stand 820 includes a hand rail 824 and two legs 826. The hand rail 824 is configured for being held by one or both hands of the patient. In some embodiments, the hand rail 824 has a length in a range from 25 inches to 40 inches, as shown in FIG. 9. The two legs 826 are attached onto the base 802 of the suspension stand 810. In some embodiments, a length of the legs 826 (such as the distance from the base 802 to the hand rail 824) matches (i.e., the same as or similar to) the height of the patient's waist off ground (hereinafter "waist height"). The length of the legs 826 can be in a range from 30 inches to 60 inches, as shown in FIG. 10. In some embodiments, the length of the legs 826 is adjustable to match waist height of various patients. The support stand 820 may be made of wood, metal, plastic, other types of materials, or some combination thereof. In some embodiments, the support stand 820 is made of tubing. In the embodiment of FIG. 8, the support stand 820 includes two legs 826. In other embodiments, the support stand 820 can include one leg or more than two legs.

Figure 12:
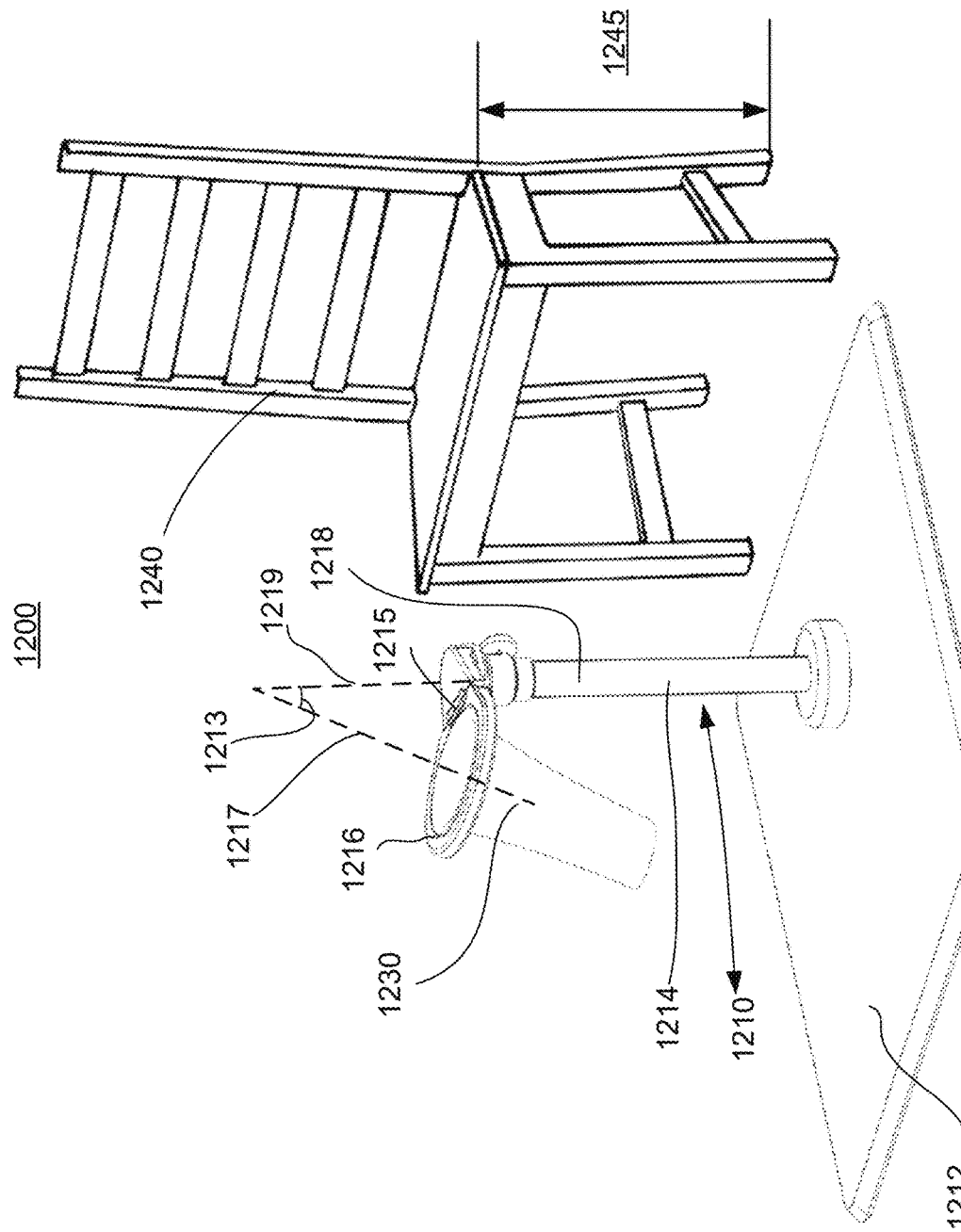
FIG. 12 illustrates a suspended sleeve assembly that allows a patient in a sitting position to step into a compression sleeve of the suspended sleeve assembly.

FIG. 12 illustrates a suspended sleeve assembly 1200 that allows a patient in a sitting position to step into a compression sleeve 1230 of the suspended sleeve assembly 1200. The suspended sleeve assembly 1200 comprises a compression sleeve 1230, a suspension stand 1210, and a chair 1240. The compression sleeve can be the compression sleeve 130 in FIGS. 1-5. A patient can sit on the chair 1240 during the processing of shaping a prosthetic socket using the suspended sleeve assembly 1200. The patient may feel more comfortable than standing.

The suspension stand 1210 includes a base 1212, a hinge 1215, a support pole 1218, and a receiver 1216 attached to the support pole 1218 through the hinge 1215. The base 1212 can be the base 102, the receiver 1216 can be the receiver 106, and the support pole 1218 can be the support pole 108. As shown in FIG. 12, the receiver 1216 is attached to the support pole 1218 through the hinge 1215. The hinge 1215 allows the receiver 1216 to be rotated in relative to the support pole 1218. As the receiver 1216 is rotated relative to the support pole 1218, an angle 1213 between a longitudinal axis 1217 of the compression sleeve 1230 and a longitudinal axis 1219 of the support pole 1218 can be changed. In some embodiments, the angle 1213 is about 45 degrees and facilitates the patient to step into the compression sleeve 1230 while sitting on the chair 1240. The patient can apply a portion of the patient's body weight to the compression sleeve 1230.

In some embodiments, the angle 1213 is determined at least based on a height 1245 of the chair 1240 changes. The height 1245 can be adjustable. With a larger height 1245, the angle 1213 is smaller and the patient applies more body weight on the compression sleeve 1230. With a smaller height 1245, the angle 1213 is larger and the patient applies less weight on the compression sleeve 1230.

Even though not shown in FIG. 12, the suspended sleeve assembly 1200 can also include a support stand, such as the support stand 820 in FIGS. 8-11.

Figure 13:
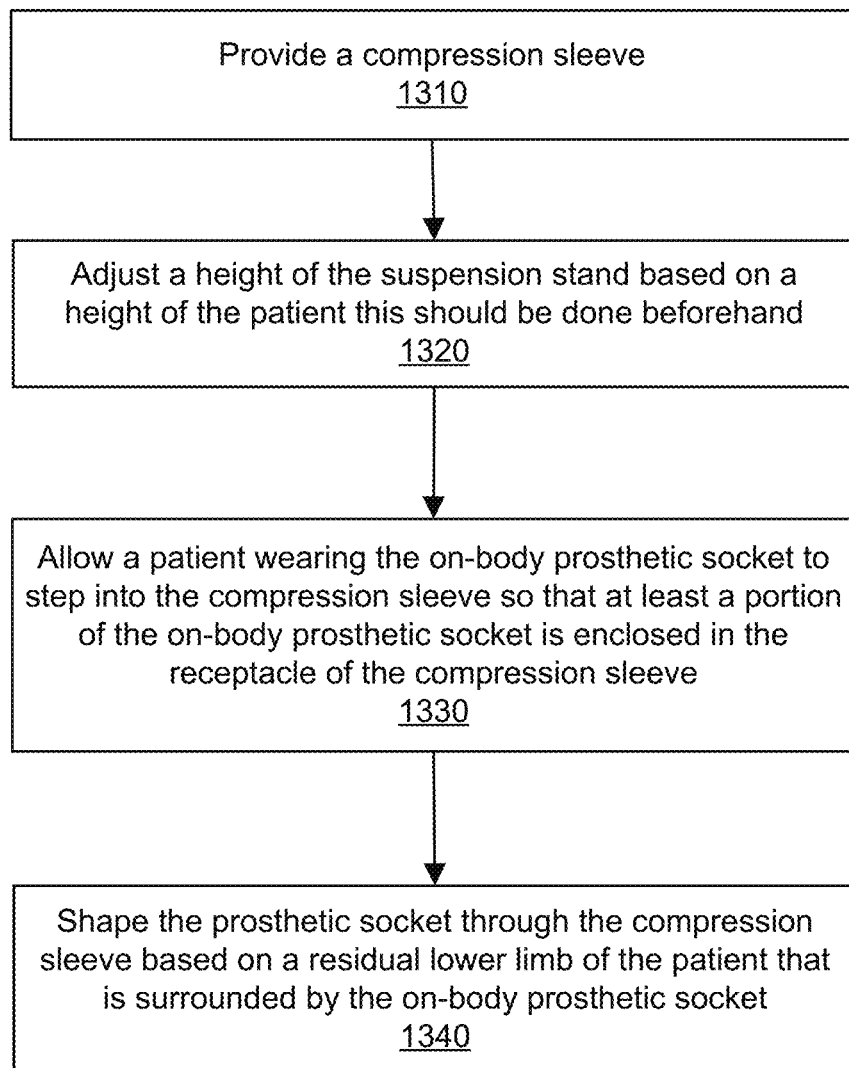
FIG. 13 is a flow chart illustrating a process for shaping an on-body prosthetic socket, in accordance with one embodiment.

FIG. 13 is a flow chart illustrating a process 1300 for shaping an on-body prosthetic socket, in accordance with one embodiment. The process 1300 may include different or additional steps than those described in conjunction with FIG. 13 in some embodiments or perform steps in different orders than the order described in conjunction with FIG. 13. The process 1300 can also be used for shaping a plaster cast, such as a wet plaster cast.

The process 1300 includes providing 1310 a compression sleeve, such as the compression sleeve 130. The compression sleeve includes an upper portion attached to a suspension stand, a lower portion that is unattached from the suspension stand, and a receptacle.

The process 1300 also includes adjusting 1320 a height of the suspension stand based on a height of the patient. The suspension stand includes a base at a lower portion of the suspension stand, a support pole attached to the base, a height adjustor attached to the support pole, and a receiver (e.g., a ring) at an upper portion of the suspension stand. In some embodiments, the height of the suspension stand is adjusted by using the height adjustor. The receiver is configured to attach the upper portion of the compression sleeve onto the suspension stand. The receiver can be attached to the support pole through a hinge that allows the receiver to be rotated in relative to the support pole. In some embodiments, the process 1300 may include rotating the receiver in relative to the support pole to allow the patient to step into the compression sleeve in a sitting position.

The process 1300 further includes allowing 1330, e.g., through the receptacle, a patient wearing the on-body prosthetic socket to step into the compression sleeve so that at least a portion of the on-body prosthetic socket is enclosed in the receptacle of the compression sleeve. The suspension stand is configured to stabilize the patient as the patient applies downward weight into the compression sleeve. The patient can be in a standing position or a sitting position. The patient in a standing position can apply full body weight to the compression sleeve. The patient in a sitting position can apply a portion of body weight to the compression sleeve.

The process further includes shaping 1340 the on-body prosthetic socket through the compression sleeve based on a residual lower limb of the patient that is surrounded by the on-body prosthetic socket. The on-body prosthetic socket can be a heat-formed socket. The shaping can be done during or after the on-body prosthetic sleeve is heated at a temperature falling in the range from 70° C. to 150° C. A prosthetist can apply a force onto the on-body prosthetic socket by hand. The compression sleeve can apply a circumferential pressure onto the on-body prosthetic socket during the shaping.

In the present disclosure, the words "a" or "an" are to be taken to include both the singular and the plural. Conversely, any reference to plural items shall include, where appropriate, the singular.

Numerous characteristics and advantages have been set forth in the preceding description, including various alternatives together with details of the structure and function of the devices and/or methods. The disclosure is intended as illustrative only and as such is not intended to be exhaustive. It will be evident to those skilled in the art that various modifications may be made, especially in matters of structure, materials, elements, components, shape, size, and arrangement of parts including combinations within the principles of the invention, to the full extent indicated by the broad, general meaning of the terms in which the appended claims are expressed. To the extent that these various modifications do not depart from the spirit and scope of the appended claims, they are intended to be encompassed therein.

I claim:

1. A suspended sleeve assembly, comprising:
   a suspension stand;

a compression sleeve comprising a receptacle comprising an upper portion configured to be attachable to the suspension stand and a lower portion;
a prosthetic socket,
wherein the compression sleeve comprises a first circumferential frame located at the upper portion of the compression sleeve,
wherein the compression sleeve is configured to enclose at least a portion of a prosthetic socket and configured to allow the prosthetic socket to be shaped based on a shape of a residual limb of a patient wearing the prosthetic socket,
wherein the receptacle is sized and configured to apply circumferential pressure onto a portion of the prosthetic socket during the shaping of the prosthetic socket,
wherein the suspension stand comprises:
a base;
a support pole attached to the base; and
a receiver attached to an upper portion of the support pole, wherein the upper portion of the compression sleeve is configured to be attached to the receiver,
wherein the prosthetic socket comprises:
a first portion configured as a conical cup comprising a material having a first pliability at between about 70° C. and 150° C.; and
a second portion configured as a base portion having a second pliability which is less than the first pliability.

2. The suspended sleeve assembly of claim 1, wherein the compression sleeve further comprises a second circumferential frame located at the lower portion of the compression sleeve, the second circumferential frame configured to secure the prosthetic socket in the compression sleeve.

3. The suspended sleeve assembly of claim 1, wherein the receptacle has a thickness of no more than three millimeters.

4. The suspended sleeve assembly of claim 1, wherein the receptacle has a closed end.

5. The suspended sleeve assembly of claim 1, wherein the receptacle comprises an elastic material selected from a group consisting of a knit fabric comprising an elastic material for applying a compressive force by stretching, a woven material configured for applying a compression force as it is stretched, diagonally woven fibers, a stretch polymer, a material configured to shrink in diameter as it is elongated, a stretch knit fabric containing spandex or rubber fibers and combinations thereof.

6. The suspended sleeve assembly of claim 1, further comprising:
a support stand configured to provide support to the patient as the patient steps into the compression sleeve.

7. The suspended sleeve assembly of claim 1, wherein the compression sleeve is configured to reduce a circumference of the conical cup when used.

8. A suspended sleeve system, comprising:
a suspension stand comprising a base and a support pole attached to the base;
a receiver attached to an upper portion of the support pole;
a compression sleeve including a receptacle having an upper portion and a lower portion, the compression sleeve is configured to be attached to the suspension stand;
a prosthetic socket comprising:
a first portion configured as a conical cup comprising a material having a first pliability at between about 70° C. and 150° C.; and
a second portion configured as a base portion having a second pliability which is less than the first pliability,
wherein the compression sleeve is configured to enclose at least a portion of a prosthetic socket and configured to allow the prosthetic socket to be shaped based at least on a shape of a residual limb of a patient wearing the prosthetic socket, and
wherein the receptacle is sized and configured to apply circumferential pressure to a portion of the prosthetic socket when being used.

9. The suspended sleeve system of claim 8, further comprising:
a support stand configured to provide support to the patient as the patient steps into the compression sleeve.

10. The suspended sleeve system of claim 8, wherein the receptacle has a thickness of less than about 3 mm.

11. The suspended sleeve system of claim 8, wherein the receptacle has a closed end.

12. The suspended sleeve system of claim 8, wherein the receptacle comprises an elastic material.

13. The suspended sleeve system of claim 8, wherein the receptacle comprises an elastic material selected from a group consisting of a knit fabric comprising an elastic material for applying a compressive force by stretching, a woven material configured for applying a compression force as it is stretched, diagonally woven fibers, a stretch polymer, a material configured to shrink in diameter as it is elongated, a stretch knit fabric containing spandex or rubber fibers and combinations thereof.

14. The suspended sleeve system of claim 8, wherein the compression sleeve is configured to reduce a circumference of the conical cup.

15. A suspended sleeve system, comprising:
a suspension stand comprising a base and a support pole attached to the base;
a receiver attached to an upper portion of the support pole;
a compression sleeve configured to be attached to the receiver and including a receptacle having an upper portion and a lower portion;
a prosthetic socket comprising:
a heat moldable first portion configured as a conical cup comprising a material having a first pliability at between about 70° C. and 150° C.; and
a second portion configured as a base portion having a second pliability which is less than the first pliability, and
wherein the compression sleeve is configured to enclose at least a portion of a prosthetic socket and configured to allow the prosthetic socket to be shaped based at least on a shape of a residual limb of a patient wearing the prosthetic socket.

16. The suspended sleeve system of claim 15, further comprising:
a support stand configured to provide support to the patient as the patient steps into the compression sleeve.

17. The suspended sleeve system of claim 15, wherein the receptacle has a thickness of less than about 3 mm.

18. The suspended sleeve system of claim 15, wherein the receptacle has a closed end.

19. The suspended sleeve system of claim 15, wherein the receptacle comprises an elastic material.

* * * * *